United States Patent
Hwang et al.

(10) Patent No.: US 8,492,304 B2
(45) Date of Patent: Jul. 23, 2013

(54) IRON COMPLEX, MANUFACTURING METHOD THEREOF AND SUPPORTED IRON OXIDE CATALYST CONSTRUCTED THEREBY

(75) Inventors: Weng-Sing Hwang, Tainan (TW); Shyh-Jiun Liu, Taipei County (TW); Chia-Hung Huang, Kaohsiung (TW); Chun-Kai Huang, Kaohsiung County (TW)

(73) Assignee: National Cheng Kung University, Tainan (TW)

( * ) Notice: Subject to any disclaimer, the term of this patent is extended or adjusted under 35 U.S.C. 154(b) by 392 days.

(21) Appl. No.: 12/650,102

(22) Filed: Dec. 30, 2009

(65) Prior Publication Data

US 2011/0160045 A1    Jun. 30, 2011

(51) Int. Cl.
*B01J 31/12* (2006.01)
*B01J 23/745* (2006.01)
*C01G 49/08* (2006.01)

(52) U.S. Cl.
USPC .................. 502/167; 502/338; 423/632

(58) Field of Classification Search
None
See application file for complete search history.

(56) References Cited

U.S. PATENT DOCUMENTS

| 4,957,939 A | 9/1990 | Gries et al. |
| 5,393,903 A | 2/1995 | Gratzel et al. |

FOREIGN PATENT DOCUMENTS

| CN | 101348240 | * | 1/2009 |
| CN | 101348240 A | * | 1/2009 |
| TW | I304357 | | 11/2005 |

OTHER PUBLICATIONS

Jiang et al. Huagong Jishu Yu Kaifa, vol. 35(7-10), 7-10, 2006.*
SNT abstract for CN 101348240.*
Liu et al., "Chelating agent-assisted heat teratment of a carbon-supported iron oxide nanoparticle caralyst for PEMFC," Chem. Commun., 2009, pp. 4809-4811.
Shyh-Jiun Liu et al., Chelating agent-assisted heat treatment of a carbon-supported iron oxide nanoparticle catalyst for PEMFC; Chemical Communications, 2009, pp. 4809-4811, vol. 32.
Martin Hermanek er al., "Thermal behavior of iron(II) oxalate dihydrate in the atmosphere of its conversion gases", *J. Mater. Chem.*, Jan. 12, 2006, pp. 1273-1280, vol. 16.
Takuya Echigo et al., "Single-crystal X-ray diffraction and spectroscopic studies on humboltine and linebergite: weak Jahn-Teller effect of Fe2+ ion", *Phys Chem Minerals*, May 7, 2008, pp. 467-475, vol. 35.

* cited by examiner

*Primary Examiner* — Yun Qian
(74) *Attorney, Agent, or Firm* — Muncy, Geissler, Olds & Lowe, PLLC (57) ABSTRACT

A manufacturing method of an iron complex is mixing ferric chloride and at least one chelating agent with a solvent, wherein $Fe^{3+}$ ions of ferric chloride is reacted with the at least one chelating agent to form an iron complex $Fe[R_1]_a[R_2]_b[H_2O]_c^{3+}$ or $Fe[R_1]_a[H_2O]_c^{3+}$, wherein the at least one chelating agent is selected from a group including ethylenediamine, 1,10-phenanthroline, 2,2'-Bipyridine, diethylenetriamine, triethylenetetraamine, phenanthroline, or bipyridine. Moreover, a method for producing an iron oxide catalyst is mixing ferric chloride, at least one chelating agent and the support with a solvent to form an iron complex, which is incorporated with the support. Following, a drying step and a heat treatment step are processed to get the iron oxide catalyst.

8 Claims, 8 Drawing Sheets

IRON COMPLEX, MANUFACTURING METHOD THEREOF AND SUPPORTED IRON OXIDE CATALYST CONSTRUCTED THEREBY

BACKGROUND OF THE INVENTION

1. Field of the Invention

The present invention relates to a complex and an application thereof and, more particularly, to an iron complex, a manufacturing method thereof, and an iron oxide catalyst constructed thereby.

2. Description of the Related Art

Catalysts are usually used to catalyze oxidation-reduction reaction. Currently, in petrochemistry and energy industry, noble metals such as Platinum (Pt) are still considered as a main source of catalysts. In petrochemistry industry, Pt catalysts are used to increase amount of petroleum. Moreover, in most of gas-cleaning facilities of vehicles, Pt catalysts are used to transfer carbon monoxide (CO) and hydrocarbon into harmless carbon dioxide and water. In energy industry, the developing fuel cell for commercial purpose is attracting more attention because a fuel cell has many advantages such as high efficiency and low emission; moreover, a fuel cell only emits harmless carbon dioxide, water and air. Therefore, the fuel cell can be a substitute for green energy wherein a great quantity of Pt or Pt on carbon-supported catalysts is applied on most of fuel cells to promote oxidation-reduction reaction wherein.

However, in the short term, using Pt catalysts or Pt on carbon support catalysts for fuel cell is practicable, but in the long term, non-noble metal catalysts must be considered as alternative catalysts for reducing manufacturing cost. If non-noble metal catalysts can be used as alternative catalysts of noble metal such as Pt catalysts or Pt on carbon-supported catalysts, the usage of catalysts can be widen. For example, manufacturing cost for membrane electrode assembly (MEA) in proton exchange membrane fuel cell (PEMFC) cannot be reduced due to the expensive cost of noble Pt catalysts used in fuel cell.

Several types of non-noble catalysts have been explored in recent years, including transition metal alloys, metal nitrides, and chalcogenides. For replacing noble catalysts by non-noble catalysts, the development of non-noble catalysts such as heat-treated Fe— and Co—N/C catalysts has led to progress in catalyst synthesis methodologies to lower manufacturing cost in fuel cell.

A conventional manufacturing method of Fe—N/C is shown in Electrochimica Acta. Vol. 42 No. 9, pp. 1379-1388, 1997 entitled "Is nitrogen important in the formulation of Fe-based catalysts for oxygen reduction in solid polymer fuel cells?." In this conventional method, 150 mg of Ferrocene, $Fe(C_5H_5)_2$, is dissolved in benzene acting as a solvent. Then, 2 gs of carbon black (XC-72) are added to the solvent and stirred to get a solution. Following, the solution is heated in order to distill the solvent to obtain an iron mixture. The iron mixture is dried at 75° C. in air to get a dried iron mixture wherein Fe loading is 2 wt %. Then, the dried iron mixture is ground before being loaded into a quartz basket while the ground iron mixture is introduced with Ar in a quartz tube at room temperature for 30 mins. The quartz tube is then placed in a split furnace preheated to 1000° C. and acetonitrile ($CH_3CN$) vapor is introduced into the quartz tube by bubbling Ar in acetonitrile maintained at room temperature. The dried iron mixture is pyrolyzed for 2 hours. The quartz tube is removed from the split furnace and cooled to room temperature before stopping the Ar gas flow so that Fe—N/C catalysts can be obtained.

In sum, the conventional manufacturing method of Fe—N/C is to reduce particle sizes of the dried iron mixture by grinding at first. Then, during pyrolysis period, acetonitrile ($CH_3CN$) vapor is introduced into the quartz tube to let Fe ions in the dried iron mixture and N ions in the acetonitrile bond together to form Fe—N/C catalysts. Therefore, the conventional manufacturing method of Fe—N/C cannot precisely control the particle size, uniformity, and dispersion of the dried iron mixture constructed the catalysts, so that surface area of the catalysts and the ability of catalysis cannot be increased. As a result, the above introduced Fe—N/C catalysts cannot actually replace the noble metal catalysts in use. Besides, the benzene solvent and acetonitrile used in the conventional manufacturing method of Fe—N/C are toxic materials resulting in harmful effect to the environment. Hence, there is a need to provide an iron complex, a manufacturing method thereof, and an iron oxide catalyst constructed thereby.

SUMMARY OF THE INVENTION

The primary objective of the present invention is to provide an iron complex, which is formed by engaging Fe ions with at least one chelating agent to increase the stability of the iron complex.

Another objective of the present invention is to provide a manufacturing method of the iron complex, by controlling combination reaction between Fe ions to let Fe ions disperse evenly.

A further objective of the present invention is to provide a manufacturing method of iron oxide obtained through the iron complex, so that a range in particle size of the iron oxide is narrow and the uniformity of particles of the iron oxide can be increased.

Still another objective of the present invention is to provide a manufacturing method of a iron oxide catalyst including the iron oxide obtained through the iron complex, so that the dispersion of particles of the obtained iron oxide in the catalyst can be enhanced.

Yet another objective of the present invention is to provide a manufacturing method of the iron oxide catalyst through the iron complex, so that surface area of the iron oxide catalyst can be increased to improve the ability of the catalysts.

Yet another objective of the present invention is to provide a manufacturing method of the iron oxide catalyst through the iron complex so that manufacturing cost of the catalyst can be reduced.

To accomplish the above objective, the present invention provides an iron complex with a form of $Fe[R_1]_a[R_2]_b[H_2O]_c^{3+}$, wherein each of the $R_1$ and the $R_2$ is selected from a group comprising ethylenediamine, 1,10-phenanthroline, 2,2'-Bipyridine, diethylenetriamine, triethylenetetraamine, phenanthroline, and bipyridine, with R1 being different from R2, and an equation of (a×the coordination number of R1)+(b×the coordination number of R2)+c=6 being held.

According to the present invention, another iron complex in the form of $Fe[R_1]_a[H_2O]_c^{3+}$ is provided, wherein the $R_1$ is selected from a group comprising ethylenediamine, 1,10-phenanthroline, 2,2'-Bipyridine, diethylenetriamine, triethylenetetraamine, phenanthroline, and bipyridine, wherein an equation of (a×the coordination number of $R_1$) +c=6 is held.

According to the present invention, a manufacturing method of an iron complex is provided, which comprises: mixing ferric chloride and at least one chelating agent with a solvent, wherein $Fe^{3+}$ ions of ferric chloride is reacted with at least one chelating agent to form an iron complex.

According to the present invention, a manufacturing method of iron oxide through an iron complex is provided, which comprises: a chelating step mixing a ferric chloride and at least one chelating agent with a solvent to form an iron complex solution, wherein $Fe^{3+}$ ions of ferric chloride is reacted with the at least one chelating agent to form an iron complex; a drying step removing the solvent from the iron complex solution to obtain a dried iron complex; and a heat treatment step executing heat treatment for the dried iron complex to form iron oxide with molecular formula $Fe_3O_4$.

According to the present invention, a manufacturing method of an iron oxide catalyst through the iron complex is provided, which comprises: a chelating step mixing a ferric chloride, at least one chelating agent, and a support with a solvent to form an iron complex solution with the support, wherein $Fe^{3+}$ ions of ferric chloride is reacted with the at least one chelating agent to form an iron complex which is incorporated with the support; a drying step removing the solvent from the iron complex solution with the support to form a dried iron complex on the support; and a heat treatment step executing heat treatment for the dried iron complex on the support to form iron oxide with molecular formula $Fe_3O_4$.

Further scope of the applicability of the present invention will become apparent from the detailed description given hereinafter. However, it should be understood that the detailed description and specific examples, while indicating preferable embodiments of the invention, are given by illustrations only, since various will become apparent to those skilled in the art from this detailed description.

BRIEF DESCRIPTION OF THE DRAWINGS

The present invention can be fully understood from the detailed description given herein below and the accompanying drawings which are given illustrations only, and thus are not limitative of the present invention, and wherein.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions that conform to specify the forces of weight, strength, and similar requirements will likewise be within the skill of the art after the following teachings of the present invention have been read and understood.

Where used in the various figures of the drawings, the same numerals that designate the same or similar parts. Furthermore, when the terms "first", "second", "third", "fourth", "fifth", "sixth", "below", and similar terms are used herein, it should be understood that these terms have reference only to the structure shown in the drawings as it would appear to a person viewing the drawings and are utilized only to facilitate describing the invention.

DETAILED DESCRIPTION OF THE INVENTION

The present invention is focused on forming an iron complex and using the iron complex as precursor for making iron oxide and a catalyst including the iron oxide and a support.

A. A Manufacturing Method of the Iron Complex of the Present Invention

The manufacturing method of the iron complex of a preferred embodiment according to the preferred teachings of the present invention includes a chelating step S1. The chelating step S1 is mixing ferric chloride ($FeCl_3$) and at least one chelating agent with a solvent to form an iron complex solution. Ferric chloride is dissolved in the solvent to get $Fe^{3+}$ ions for reacting with the at least one chelating agent, so that $Fe^{3+}$ ions can be engaged in the at least one chelating agent to form the iron complex in forms, $Fe[R_1]_a[R_2]_b[H_2O]_c^{3+}$ or $Fe[R_1]_a[H_2O]_c^{3+}$, wherein both of $R_1$ and $R_2$ represent the at least one chelating agent of the present invention; "a," "b," and "c" respectively represent mole ratio of $R_1$, $R_2$, and $H_2O$ to Fe, which can be denoted as $R_1$/Fe, $R_2$/Fe, and $H_2O$/Fe. The solvent can be selected from water, ethanol, ether or acetonein, and is water or ethanol-water solution preferably. The at least one chelating agent is selected from consists of ethylenediamine ($NH_2CH_2CH_2NH_2$), 1,10-phenanthroline ($C_{12}H_8N_2$), 2,2'-Bipyridine ($C_{10}H_8N_2$), diethylenetriamine ($NH_2CH_2CH_2NHCH_2CH_2NH_2$), triethylenetetraamine ($NH_2CH_2CH_2NHCH_2CH_2NHCH_2CH_2NH_2$), phenanthroline ($C_{12}H_8N_2$), and bipyridine ($C_{10}H_8N_2$). For simplifying description, the at least one chelating agent with abbreviated form is shown as below. Ethylenediamine is denoted as "en", 1,10-phenanthroline is denoted as "phen", and 2,2'-bipyridine is denoted as "bpy" with the coordination number of 2; Diethylenetriamine is denoted as "dien" with the coordination number of 3; Triethylenetetraamine is denoted as "trien" with the coordination number of 4. So far, the manufacturing method of the iron complex can be completed to get the iron complex of the present invention.

If the ferric chloride and the two chelating agents $R_1$ and $R_2$ are mixed with the solvent, the iron complex is in the form $Fe[R_1]_a[R_2]_b[H_2O]_c^{3+}$.

Furthermore, the chelating agent $R_1$ is different from the chelating agent $R_2$, and the coordination number of Fe is 6. The number of "a," "b," and "c" in the form of the iron complex may be obtained through formula (a) as the following:

$$(a \times \text{the coordination number of } R_1) + (b \times \text{the coordination number of } R_2) + c = 6. \quad (a)$$

For example, ethylenediamine with the coordination number of 2 is used as the chelating agent $R_1$, and diethylenetriamine with the coordination number of 3 is used as the second chelating agent $R_2$. Both of the mole ratios "a" and "b" are 1 and the mole ratio "c" of $H_2O$ is 1. Because the total number of the coordination number is 6, the iron complex is shown in the form of $Fe[en][dien][H_2O]^{3+}$. In detail, the chelating step S1 is adding stoichiometric amounts of the at least one chelating agent to the ferric chloride by being stirred into the solvent, so that $Fe^{3+}$ ions dissolved from the ferric chloride solution can be reacted with the at least one chelating agent to form iron complex of the present invention in a general form of $Fe[R_1]_a[R_2]_b[H_2O]_c^{3+}$.

In addition, if ferric chloride and the chelating agent $R_1$ are mixed with the solvent, the iron complex is in the form of $Fe[R_1]_a[H_2O]_c^{3+}$. The number of "a" and "c" in the form of the iron complex may be obtained through formula (b) as the following:

$$(a \times \text{the coordination number of } R_1) + c = 6. \quad (b)$$

For example, ethylenediamine with the coordination number of 2 is used as the chelating agent $R_1$. The mole ratio "a" is 2 and the mole ratio "c" is 2. Because the total number of the coordination number is 6, the iron complex is shown in the form of $Fe[en]_2[H_2O]_2^{3+}$. The other example is that diethylenetriamine with the coordination number of 3 is used as the chelating agent $R_1$. The mole ratio "a" is 1 and the mole ratio "c" is 3. Because the total number of the coordination number is 6, the iron complex is shown in the form of $Fe[dien][H_2O]_3^{3+}$. Besides, the mole ratio "a" also can be 2, to get iron complex in the form of $Fe[dien]_2^{3+}$. Another example is that triethylenetetraamine with the coordination number of 3 is used as the chelating agent $R_1$. The mole ratio "a" is 1 and the mole ratio "c" is 2. The iron complex is shown in the form of $Fe[trien][H_2O]_2^+$. Therefore, the manufacturing method of the iron complex can be completed to form the iron complex of the present invention in a general form of $Fe[R_1]_a[H_2O]_c^{3+}$.

Furthermore, the manufacturing method of the iron complex according to the preferred teachings of the present invention further includes continuously stirring during mixing the ferric chloride and the at least one chelating agent with the solvent. More particularly, the solvent is under stirring condition until all of the ferric chloride and the at least one chelating agent are added into the solvent to get a well mixed solution. After thoroughly stirred, the solution is sonicated for 24 hours to let the solution be more uniformly blended.

According to the description above, by selecting various chelating agents, different forms of the iron complex can be obtained. The iron complex can further be used as precursor.

Moreover, in the previously disclosed manufacturing method of the iron complex of the preferred embodiment according to the preferred teachings of the present invention has $Fe^{3+}$ as a central cation of the iron complex, which has a coordination number of 6. The surrounding ligands are the at least one chelating agent. The at least one chelating agent with nitrogen donor atoms gives tstable low-spin, octahedral, or distorted octahedral complexes.

Complex is a structure consisting of a central atom or ion, bonded to a surrounding array of molecules or anions. The molecules or anions surrounding the central atom are called ligands. Ligands are generally bound to the central atom by a coordinate covalent bond (donating electrons from a lone electron pair into an empty metal orbital), and are thus said to be coordinated to the atom. Ligands can be divided into monodentate ligands such as $NH_3$, $F^-$, $Cl^-$, $CO$, $CN^-$ or $H_2O$ etc. and polydentate ligands. Complexes of polydentate ligands are called chelate complexes. They tend to be more stable than complexes derived from monodentate ligands. This enhanced stability, the chelate effect, is usually attributed to effects of entropy, which favors the displacement of many ligands by one polydentate ligand. Therefore, selection of the at least one chelating agent can be changed according to the coordination number of the at least one chelating agent. Types of the at least one chelating agent are not limited to chelating agents described above.

B. Iron Complex of the Present Invention

According to the manufacturing method of iron complex as described above, one general form of the iron complex is $Fe[R_1]_a[R_2]_b[H_2O]_c^{3+}$, wherein both of the chelating agents $R_1$ and $R_2$ are selected from ethylenediamine, 1,10-phenanthroline, 2,2'-Bipyridine, diethylenetriamine, triethylenetetraamine, phenanthroline, or bipyridine. The chelating agent $R_1$ is different from the chelating agent $R_2$. According to the formula (a). Therefore, the iron complex with several kinds of combination can be obtained such as $Fe[en][dien][H_2O]^{3+}$ etc.

In addition, according to the manufacturing method of the iron complex as described above, the other general form of iron complex is $Fe[R_1]_a[H_2O]_c^{3+}$, wherein the chelating agent $R_1$ is selected from ethylenediamine, 1,10-phenanthroline, 2,2'-Bipyridine, diethylenetriamine, triethylenetetraamine, phenanthroline, or bipyridine. According to the formula (b), iron complex with several kinds of combination can be obtained such as $Fe[en][H_2O]_4^{3+}$, $Fe[en]_2[H_2O]_2^{3+}$, $Fe[trien][H_2O]_2^{3+}$, and $Fe[dien][H_2O]_3^{3+}$ etc.

The manufacturing method of the iron complex according to the teachings of the present invention can get the uniform iron complex. The iron complex can be further used on manufacturing iron oxide to improve magnetic strength of iron oxide.

Figure 1:
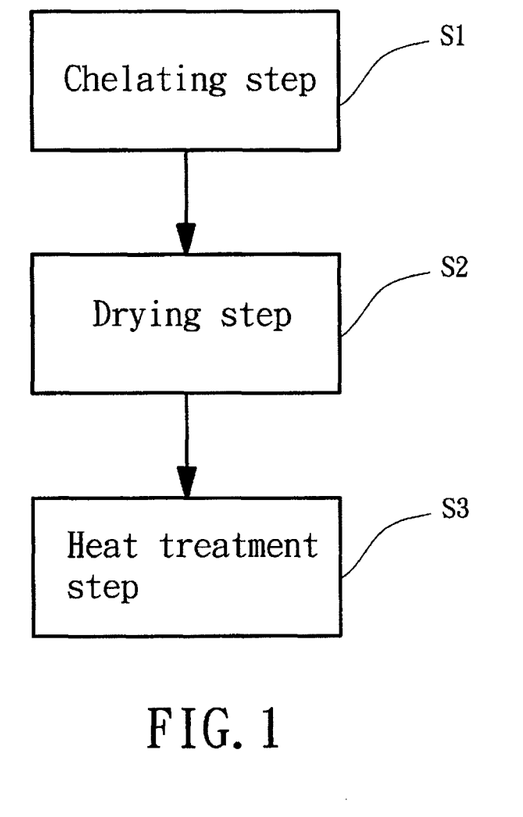
FIG. 1 is a flow chart of a manufacturing method of an iron oxide in accordance with a preferred embodiment of the present invention.

C. A Manufacturing Method of Iron Oxide Through at Least One of the Above Iron Complexes:

A manufacturing method of iron oxide through an iron complex of a preferred embodiment according to the preferred teachings of the present invention is shown in FIG. 1. The manufacturing method of iron oxide through the iron complex comprises a chelating step S1, a drying step S2, and a heat treatment step S3 to form iron oxide.

The chelating step Si is mixing ferric chloride ($FeCl_3$) and at least one chelating agent with a solvent to form an iron complex solution. Ferric chloride is dissolved in the solvent to get $Fe^{3+}$ ions for reacting with the at least one chelating agent, so that $Fe^{3+}$ ions can be engaged in the at least one chelating agent to form the iron complex. The chelating step S1 of the manufacturing method of iron oxide through the iron complex is the same as the chelating step S1 of the manufacturing method of the iron complex and, thus, not described in detail to avoid redundancy. The chelating step Si is used for the at least one chelating agent to confine Fe ions so that bonding between Fe ions is getting more difficult. Therefore, the growth of iron can be controlled to form the iron complex suspensed in the solvent uniformly. As a result, the well-distributed iron complex solution can be obtained.

The drying step S2 is to remove the solvent from the iron complex solution. In the preferred form, the iron complex solution is dried by an evaporator under vacuum condition to obtain a dried iron complex.

The heat treatment step S3 is subjected to execute a heat treatment for the dried iron complex to get iron oxide. In detail, the preferred embodiment according to the preferred teachings of the present invention is putting the dried iron complex in a nitrogen atmosphere and then the heat treatment is processed for pyrolysis of the dried iron complex. It is preferable to limit the temperature of the heat treatment between 800 and 900° C., and the best temperature is at 850° C. The time period of the heat treatment is preferably between 1 to 4 hours. After completing the heat treatment step S3, iron oxide can be formed. So far, the manufacturing method of iron oxide through the iron complex of the present invention can be completed. By the heat treatment step S3 of the present invention, the dried iron complex obtained by pyrolysis can be transformed to iron oxide (magnetite) with molecular formula $Fe_3O_4$, which also can be formulated as $FeO \cdot Fe_2O_3$. Iron oxide ($Fe_3O_4$) contains one $Fe^{2+}$ and two $Fe^{3+}$ ions. $Fe_3O_4$ exhibits permanent magnetism and is ferromagnetic. $Fe_3O_4$ is an electrical conductor with a conductivity significantly higher than $Fe_2O_3$. $Fe_3O_4$ and has a cubic inverse spinel structure which consists of a cubic close packed array of oxide ions where all of the $Fe^{2+}$ ions occupy half of the octahedral sites and the $Fe^{3+}$ are split evenly across the remaining octahedral sites and the tetrahedral sites. Therefore, according to the manufacturing method of iron oxide through the iron complex of the present invention, iron oxide ($Fe_3O_4$) with uniform particle size can further enhance magnetic and active site of iron oxide.

Furthermore, after pyrolysis of the dried iron complex to form the iron oxide, the iron oxide is preferably allowed to cool to the room temperature in an environment of nitrogen so that particle size of the iron oxide can be more uniform and the stability of iron oxide can be improved.

According to the manufacturing method of iron oxide through the iron complex as described above, in the chelating step S1, Fe ions can be confined by the at least one chelating agent to reduce bonding ability between central Fe ions of iron complex to let the iron complex be well distributed in the solvent. Therefore, the bonding number of central Fe ions can be controlled to improve dispersion and uniformity of iron oxide particles. Iron oxide of the present invention can be used to produce high magnetic nanofuild. By using iron oxide in various magnet induction system to achieve magnetic response ability with high efficiency, the iron oxide can be used on related industries such as biological sensibility, MRI development, heat treat for tumor, magnet induction, drug delivery, magnetic material, electromagnetic wave proof, and catalysis etc. Iron oxide can also be combined with instruments for medical use to achieve the purpose of synchronizing diagnosis and therapy.

Furthermore, iron complex of the present invention can be further used as precursor for production of an iron oxide catalyst. In detail, the iron complex is incorporated onto a support to form the iron oxide catalyst to increase surface area of catalyst and ability of loading. The coordination number of iron complex affects the formation of the active site for oxygen reduction in PEMFC so that the ability of catalyst will also be affected.

Figure 2:
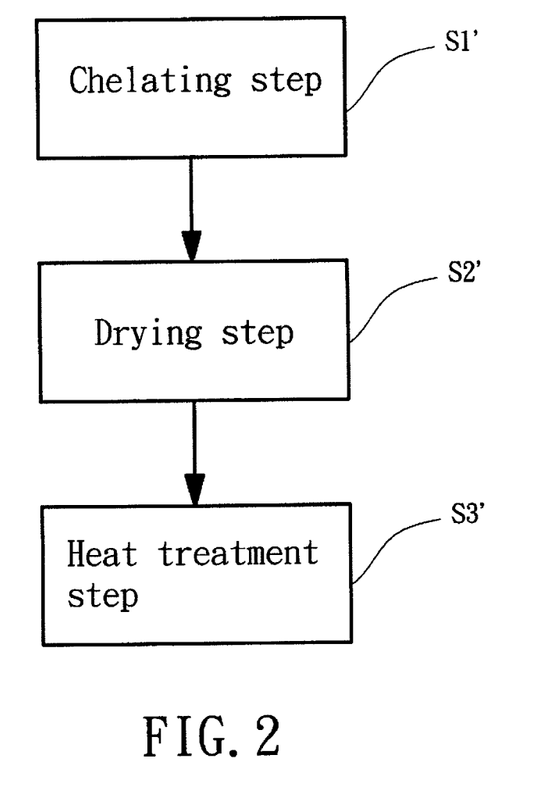
FIG. 2 is a flow chart of a manufacturing method of iron oxide catalysts including the iron oxide in accordance with the preferred embodiment of the present invention.

D. A Manufacturing Method of an Iron Oxide Catalyst Through the Iron Complex of the Present Invention:

A manufacturing method of an iron oxide catalyst through the iron complex of a preferred embodiment according to the preferred teachings of the present invention is shown in FIG. 2. The manufacturing method of the iron oxide catalyst through the iron complex comprises a chelating step S1', a drying step S2', and a heat treatment step S3' to form the iron oxide catalyst.

The chelating step S1' is mixing ferric chloride ($FeCl_3$), at least one chelating agent, and a support with a solvent to form an iron complex solution with the support. Ferric chloride is dissolved in the solvent to get $Fe^{3+}$ ions for reacting with the at least one chelating agent, so that $Fe^{3+}$ ions can be engaged in the at least one chelating agent to form the iron complex. Then, the iron complex is incorporated onto the support. The chelating step S1' of the manufacturing method of the iron oxide catalyst through iron complex is the same as the chelating step S1 of the manufacturing method of iron complex and, thus, not described in detail to avoid redundancy.

Iron complex is in the form of $Fe[R_1]_a[R_2]_b[H_2O]_c^{3+}$ or $Fe[R_1]_a[H_2O]_c^{3+}$ with $Fe^{3+}$ acting as its central cation, which has a coordination number of 6. The choice of an appropriate chelating agent and the coordination number of nitrogen of the chelating agent to iron is the most important factor in controlling the formation of active centre in the iron oxide catalyst. In the preferred form, the coordination number of the at least one chelating agent to iron is 4 or 5. Therefore, when iron complex is in the form $Fe[R_1]_a[R_2]_b[H_2O]_c^{3+}$ and the chelating agent $R_1$ is different from the chelating agent $R_2$, the number of (a×the coordination number of $R_1$) plus (b×the coordination number of $R_2$) is preferred to be 4 or 5. Thus, both of the chelating agents $R_1$ and $R_2$ are better to be chelating agents with bidentate chelating ligand or a combination with one bidentate chelating ligand and one tridentate chelating ligand. The at least one chelating agent of the present invention with bidentate chelating ligand is better to be selected from ethylenediamine, 1,10-phenanthroline, or 2,2'-Bipyridine. The at least one chelating agent of the present invention with tridentate chelating ligand is better to be diethylenetriamine. The at least one chelating agent of the present invention with tetradentate chelating ligand is better to be triethylenetetraamine. For example, the chelating agent $R_1$ is ethylenediamine and the chelating agent $R_2$ is diethylenetriamine, and the iron complex is in the form of $Fe[en][dien][H_2O]^{3+}$, wherein the coordination number of the at least one chelating agent to iron is 5.

In addition, if formation of the iron complex is $Fe[R_1]_a[H_2O]_c^{3+}$, the number of (a×the coordination number of $R_1$) is better to be 4 or 5 and the chelating agent $R_1$ is better to be two same bidentate chelating ligands or one tetradentate chelating ligand. For example, the chelating agent $R_1$ is ethylenediamine, which has coordination number of 2 and the coordination number of Fe is 6, so that remaining coordination number of Fe is filled by $H_2O$, which is monodentate chelating ligand. Therefore, the iron complex is shown in the form of $Fe[en]_2[H_2O]_2^{3+}$, wherein the coordination number of chelating agent to iron is 4. Besides, according to the formula (b), various forms of the iron complex can be formed by selection of the at least one chelating agent.

Furthermore, the support is preferably selected from various porous materials, which are further divided into two types, microporous materials and macroporous materials. Microporous materials include powder of silica, carbon black, zinc oxide, and silicon carbide etc. Macroporous materials include diatomite, floatstone, alumina, active carbon, and silica etc. The support used in the present invention is better to be carbon black and silica etc. According to the preferred teachings of the present invention, carbon black is used as the support of iron oxide to increase surface area and dispersion of iron oxide. Furthermore, by using carbon black as the support, amount of catalyst used in fuel cell can be reduced to lower manufacturing cost. Sequence for adding ferric chloride, at least one chelating agent, and carbon black can be changed. Ferric chloride ($FeCl_3$) and the at least one chelating agent are added to the solvent, and carbon black can be loaded therebefore or thereafter. Furthermore, Ferric chloride ($FeCl_3$), the at least one chelating agent, and the support also can be added into the solvent in the same time. Therefore, Fe ions of ferric chloride can be reacted with the at least one chelating agent to form the iron complex which is incorporated in surface of the support so that dispersion of the iron complex can be enhanced. Following, the drying step S2 can be processed. Iron complex is incorporated onto the support, carbon black, and carbonized by heat treatment to obtain the iron oxide catalyst to confine the growth of iron oxide within an area wherein the Iron complex connects with the carbon black.

Moreover, it is better to preclean the support by hydrochloric acid (HCl) to remove metal impurity therein before the support is added into the solvent. Then, because chloride will affect formation of particle size of iron oxide, deionized water is used to remove chloride in the support so that iron oxide can be well distributed in the support. Moreover, in order to increase dispersion and avoid agglomeration of the support in the solvent, the support is added to ethanol and mix well first before adding into the solvent. Therefore, iron oxide after pyrolysis can be dispersed uniformly in the support to get the iron oxide catalyst with narrow distribution of nanoparticles.

As described above, in the chelating step S1', ferric chloride, the at least one chelating agent, and the support are added into the solvent under continuously stirring in the solvent to get an iron complex solution with the support. Then, it is preferable to sonicate the iron complex solution with the support for 24 hours to enhance uniformity of the solution with the support.

Referring to FIG. 2 again, regarding the drying step S2' of the manufacturing method of the iron oxide catalyst through the iron complex according to the preferred teachings of the present invention, the solvent is preferably removed from the iron complex solution with the support under vacuum condition to form a dried iron complex on the support.

Regarding the heat treatment step S3' of the present invention, the dried iron complex on the support is subjected to heat treatment. After pyrolysis, an iron oxide catalyst can be formed. In detail, in this embodiment, the dried iron complex on the support is subjected to heat treatment in a nitrogen atmosphere. It is preferable to limit the temperature of heat treatment between 800 and 900° C.; more particularly, the temperature is at 850° C. Time period of heat treatment is better between 1 to 4 hours. After completing heat treatment, the dried iron complex on the support can be obtained. The loading of Fe in iron oxide with respect to the support is about 2%. So far, the manufacturing method of the iron oxide catalyst through the iron complex of the present invention can be completed. According to the preferred teachings of the present invention, nanoparticles of the iron oxide catalyst is uniformly dispersed with narrow distribution of particle size. During heat treatment, the iron complex can be incorporated in the support to form several active sites; therefore, the ability of catalysis can be enhanced.

In addition, according to the preferred teachings of the present invention, after completing the heat treatment step S3', the iron oxide catalyst is allowed to cool to the room temperature in an environment of nitrogen. Following is substantially the same as described above and therefore not described in detail to avoid redundancy.

E. Detail Embodiments of the Manufacturing Method of the Iron Oxide Catalyst According to the Preferred Teachings of the Present Invention:

The manufacturing method of the iron oxide catalyst of a first example according to the preferred teachings of the present invention is illustrated as the following. Preferably, carbon black is used as the support to form the iron oxide catalyst. For following easy description, iron oxide with carbon black as the support is abbreviated as $Fe_3O_4$/C-y, wherein "y" represents types of the at least one chelating agent. The coordination number of the at least one chelating agent to Fe can be 2 to 6 etc, and preferably, the coordination number of the at least one chelating agent to Fe is 4 or 5. According to types of the at least one chelating agent, which have various coordination numbers, several kinds of iron complexes can be formed.

The manufacturing method of the iron oxide catalyst of the first example according to the preferred teachings of the present invention, during the chelating step Si', ethylenediamine is used as a chelating agent and ethanol-water (1:1) solution is used as a solvent. Carbon black, Vulcan XC-72, with 450 mg is used as a support. Ratio of the chelating agent to Fe is 2:1. The solvent is under continuously stirring condition until all of ferric chloride and at least one chelating agent are added into the solvent and mixed well to form iron complex of $Fe[en]_2[H_2O]_2^{3+}$. Moreover, the support is cleaned by 6M of HCl and deionized water to remove impurities from carbon black and then the support is mixed with 10 ml of ethanol before adding into the solvent to form an iron complex solution with the support. 0.22 mmol of iron complex of $Fe[en]_2[H_2O]_2^{3+}$ is incorporated in the carbon black. For thoroughly mixed, the iron complex solution with the support is sonicated for 24 hours to get a paste. The loading of Fe with respect to carbon black is about 2%. Following, the drying step S2' is processed under vacuum condition to remove the solvent from the paste to form a dried sample. Finally, during the heat treatment step S3', the dried sample is subjected to heat treatment at 850° C. in a nitrogen atmosphere. After 4 hours of pyrolysis, the dried sample is allowed to cool to the room temperature in an environment of nitrogen. The resulting material is an iron oxide catalyst denoted as $Fe_3O_4$/C. Chemical compositions of the iron oxide catalyst are determined using ICP-AES. Weight percentages of Fe is 2.32% for the iron oxide catalyst of the first embodiment. For the convenience of the following description, the iron oxide catalyst of the first embodiment is marked "A" and is abbreviated as $Fe_3O_4$/C-en. According to the mole ratio of the at least one chelating agent to Fe, the forming structure of iron oxide after completing the heat treatment step S3' will be different. The use of iron complex as precursor enhances the activity of the iron oxide catalyst and the ability of catalysis, indicating that the at least one chelating agent takes part in the formation of the active centre.

For comparison, an iron oxide catalyst of a second example is made by the same method as described in the first example and therefore not described in detail to avoid redundancy. The only difference is that, in the second example, a mole ratio of the chelating agent to Fe is 1:1 in the chelating step S1' to form iron complex of $Fe[en][H_2O]_4^{3+}$. After completing the heat treatment step S3', the iron oxide catalyst with structure of iron oxide being hematite($Fe_2O_3$) is formed. For the convenience of the following description, another iron oxide catalyst is marked "B" and is abbreviated as $Fe_2O_3$/C. Weight percentages of Fe is 2.54% for $Fe_2O_3$/C catalyst.

The manufacturing method of the iron oxide catalyst of a third example according to the preferred teachings of the present invention is the same as the first embodiment as described above and therefore not described in detail to avoid redundancy. The only difference between the third and the first examples is that the at least one chelating agent used in the third example is diethylenetriamine to form iron complex of $Fe[dien][H_2O]_3^{3+}$ wherein mole ratio of the chelating agent to Fe is 1:1. For the convenience of the following description, the iron oxide catalyst of the third example is marked "C" and is abbreviated as $Fe_3O_4$/C-dien.

The manufacturing method of the iron oxide catalyst of a fourth example according to the preferred teachings of the present invention is the same as the first embodiment as described above and therefore not described in detail to avoid redundancy. The only difference between the fourth and first examples is that the at least one chelating agent used in the fourth example is triethylenetetraamine to form iron complex of $Fe[trien][H_2O]_2^{3+}$ wherein a mole ratio of the chelating agent to Fe is 1:1. For the convenience of the following description, the iron oxide catalyst of the fourth example is marked "D" and is abbreviated as $Fe_3O_4$/C-trien. Weight percentages of Fe is 2.32% for $Fe_3O_4$/C-trien catalyst by ICP-AES.

The manufacturing method of the iron oxide catalyst of a fifth example according to the preferred teachings of the present invention is the same as the first embodiment as described above and therefore not described in detail to avoid redundancy. The only difference between the fifth and first examples is that the at least one chelating agent used in the fifth example is ethylenediamine and diethylenetriamine to form iron complex of $Fe[en][dien][H_2O]^{3+}$ wherein a mole ratio of each chelating agent to Fe is 1:1. For the convenience of the following description, the iron oxide catalyst of the fifth example is marked "E" and is abbreviated as $Fe_3O_4$/C-en-dien. Weight percentages of Fe is 2.48% for $Fe_3O_4$/C-en-dien catalyst by ICP-AES.

The manufacturing method of the iron oxide catalyst of a sixth example according to the preferred teachings of the present invention is the same as the first embodiment as described above and therefore not described in detail to avoid redundancy. The only difference between the sixth and first examples is that the at least one chelating agent used in the sixth example is diethylenetriamine to form iron complex of $Fe[dien]_2^{3+}$ wherein a mole ratio of the chelating agent to Fe is 2:1. Weight percentages of Fe is 2.72% for the iron oxide catalyst of the sixth example by ICP-AES.

Moreover, the iron oxide catalyst of the present invention can be used in proton exchange membrane fuel cell (PEMFC). The iron oxide catalyst is applied on Nafion® 212 membrane to make membrane electrode assembly (MEA). In detail, $Fe_3O_4$/C catalyst is added into a mixed solution with a solvent such as ethanol or isopropyl alcohol and 5 wt. % of Nafion® solution. Following, the mixed solution with $Fe_3O_4$/C catalyst is sprayed on a substrate such as carbon clothes and then membrane electrode assembly (MEA) is integrated between two carbon clothes by conventional hot press for 90 seconds. The temperature of hot press is around 135° C. The pressure of hot press is around 50 kg/cm². $Fe_3O_4$/C catalyst of the present invention is better to be used as cathode catalyst.

F. X-ray Diffractometer (XRD)

Figure 3:
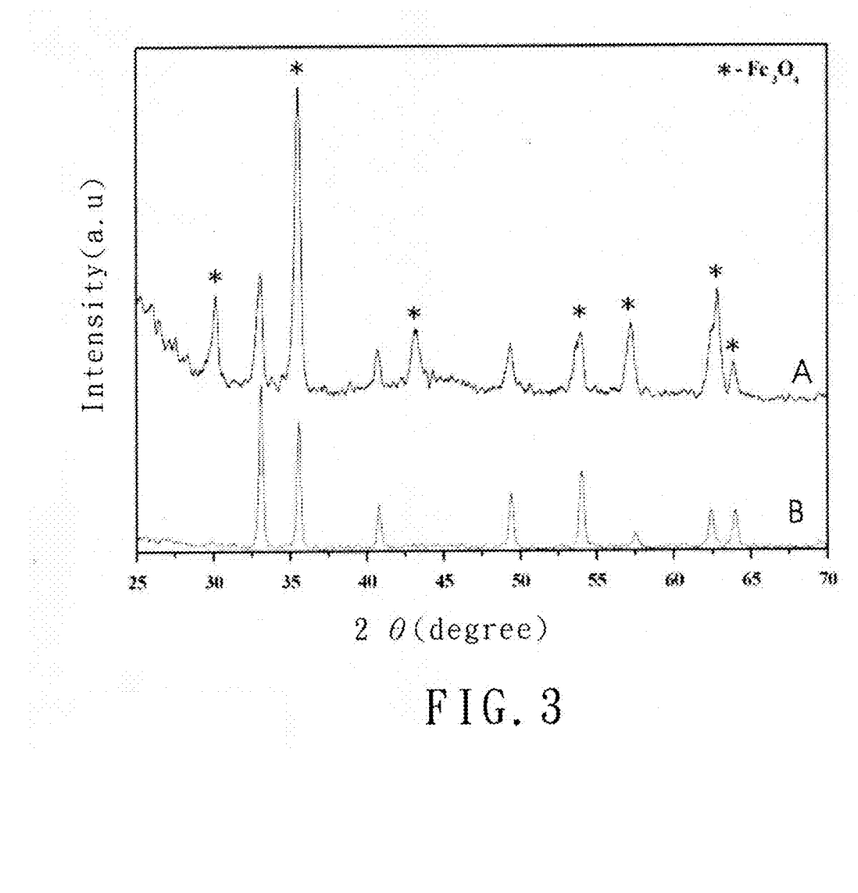
FIG. 3 is a XRD graph of the iron oxide catalysts of FIG. 2 in accordance with the preferred embodiment of the present invention.

Referring to FIG. 3, the XRD patterns of the iron oxide catalyst are shown. Ethylenediamine is used as the chelating agent wherein mole ratio of the chelating agent to Fe is 2:1 and 1:1 respectively to obtain "A" catalyst and "B" catalyst as described above. All the diffraction peaks in "B" catalyst can be indexed to hematite $Fe_2O_3$. The peaks at 2θ=24.1°, 33.2°, 35.6°, 40.8°, 49.5°, 54.1°, 57.6°, 62.5°, and 63.9° correspond to 012, 104, 110, 113, 024, 116, 018, 214, and 300 planes of the rhombohedral space group R3c, respectively. This suggests that the incorporated iron complex of $Fe[en][H_2O]_4^{3+}$ was transformed to hematite during the heat treatment step S3'. The X-ray diffraction pattern of "A" catalyst revealed that magnetite ($Fe_3O_4$) co-existed with hematite ($Fe_2O_3$). The first peak at the low 2θ range (2θ=25°) was associated with the support, XC-72 carbon black. The peaks at 2θ=30.9°, 35.4°, 43.05°, 53.4°, 56.9°, 62.5°, and 65.4° respectively correspond to 220, 311, 400, 422, 511, 440, and 531 planes of the cubic space group Fd3m, which can be indexed to magnetite $Fe_3O_4$.

G Morphology Observation by High-Resolution Transmission Electron Microscope (HRTEM)

Figure 4A:
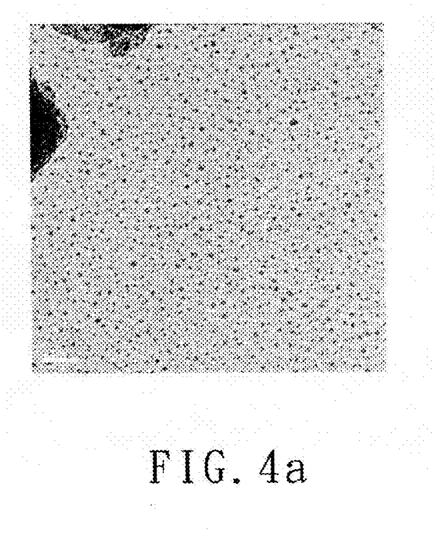
FIG. 4a is a HRTEM image of an iron oxide catalyst "A" ($Fe_3O_4$/C-en) of the iron oxide catalysts by using ethylenediamine as a chelating agent at low magnification in accordance with a first example of the present invention.
Figure 4B:
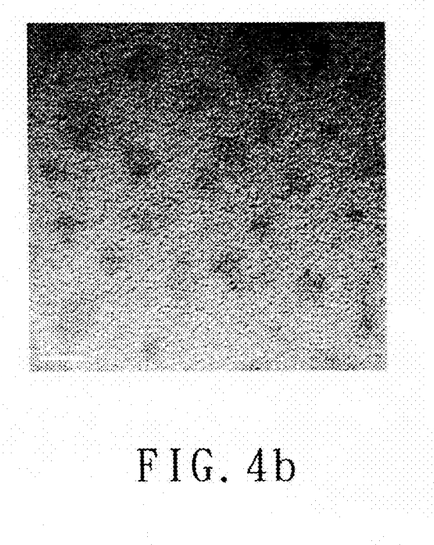
FIG. 4b is a HRTEM image of the iron oxide catalyst "A" ($Fe_3O_4$/C-en) of the iron oxide catalysts by using ethylenediamine as the chelating agent at high magnification in accordance with the first example of the present invention.
Figure 5A:
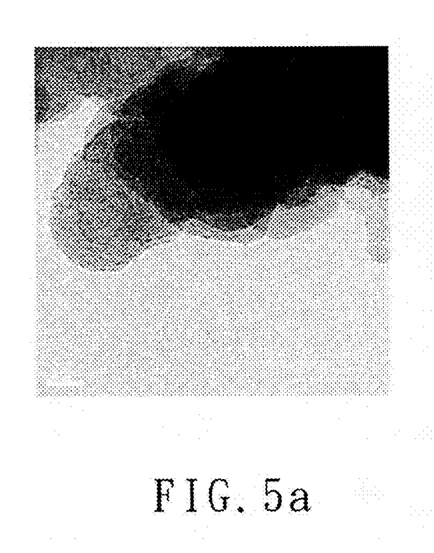
FIG. 5a is a HRTEM image of the iron oxide catalyst "B" ($Fe_2O_3$/C) of the iron oxide catalysts by using ethylenediamine as the chelating agent at low magnification in accordance with a second example of the present invention.
Figure 5B:
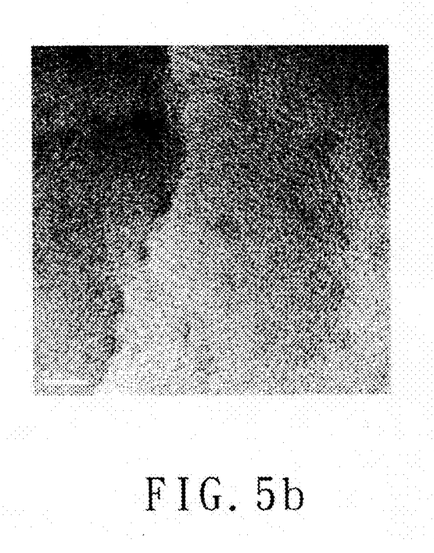
FIG. 5b is a HRTEM image of the iron oxide catalyst "B" ($Fe_2O_3$/C) of the iron oxide catalysts by using ethylenediamine as the chelating agent at high magnification in accordance with the second example of the present invention.

From morphology check by high-resolution transmission electron microscope (HRTEM), dispersion of iron oxide on the support can be observed and particle size of iron oxide can be measured. Referring to FIGS. 4a and 5a, the typical HRTEM image of the iron oxide catalyst at low magnification is shown. Referring to FIGS. 4b and 5b, the typical HRTEM image of the iron oxide catalyst at high magnification is shown. Amorphous carbon black appears as gray areas and iron oxide particles appears as black particles. FIGS. 4a-5b show that the iron oxide nanoparticles of the iron oxide catalyst are monodispersed and well distributed. Due to the high temperature heat treatment, particle size distribution of the iron oxide is in the range of 2 and 5 nm. The mean particle size is about 3 nm. Referring to FIGS. 4a and 4b, particle size distribution of "A" catalyst is in the range of 1.5 and 5 nm. The mean particle size is about 2.04 nm. Referring to FIGS. 5a and 5b, particle size distribution of "B" catalyst is in the range of 1.2 and 3.5 nm. The mean particle size is about 2.47 nm. From comparison of particle sizes between "A" catalyst and "B" catalyst, result indicates that the mole ratio of the at least one chelating agent to Fe takes part in the formation of particle size.

H. Cyclic Voltammograms (CV)

Cyclic voltammetry (CV) curves between −0.2 and 1.0 V vs Ag/AgCl electrode is recorded for the iron oxide catalyst ("A" and "B" catalysts) prepared in the present invention. Testing sample is prepared by mixing 20 mg of the iron oxide catalyst, 120 µl ethanol, 20 µl and 5 wt. % commercial 5 wt. % of Nafion® solution together and sonicated for 30 mins to get a paste solution. Following, around 25 µl of the paste solution is coated on a carbon electrode (area around 0.066 cm²) and then dried in room temperature to form a thin film on surface of the carbon electrode. Electrical testing is processed in 80 ml, 0.5M of sulfuric acid ($H_2SO_4$) with 25° C. Before electrical testing, activity of the carbon electrode is activated under flowing nitrogen.

Figure 6:
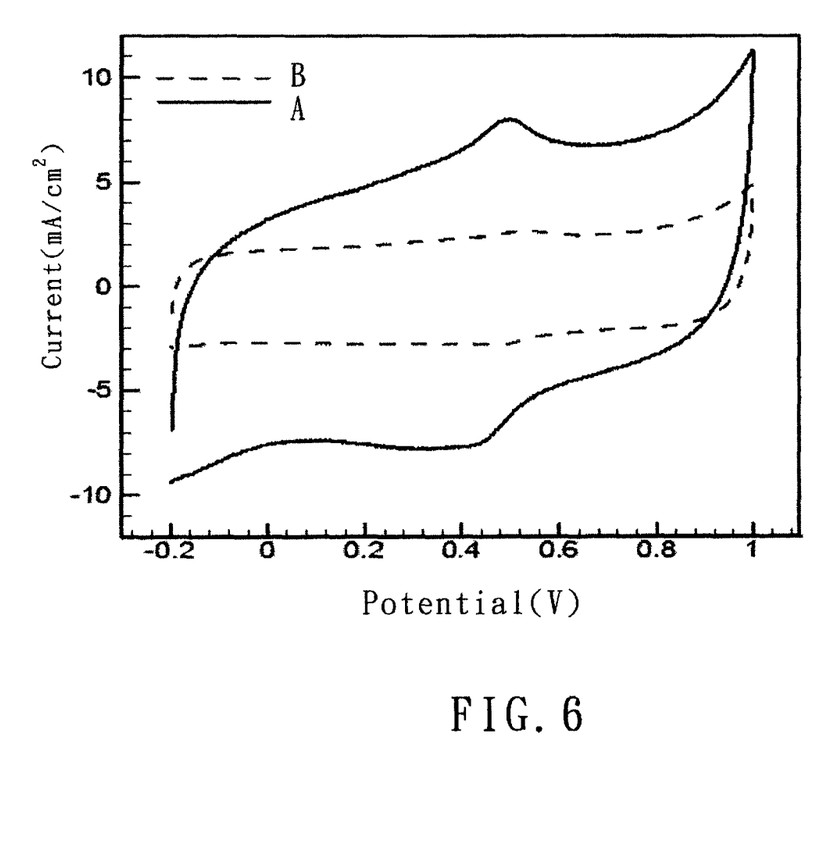
FIG. 6 is sets of cyclic voltammographs (CV) of the iron oxide catalyst in accordance with the first and second examples of the present invention.

Sets of cyclic voltammographs are shown in FIG. 6. In the first example according to the preferred teachings of the present invention, specific active surface area of the "A" catalyst ($Fe_3O_4$/C-en) is larger than "B" catalyst ($Fe_2O_3$/C-en). As a result, the ability of catalysis for "A" catalyst is better than "B" catalyst therefore.

Figure 7:
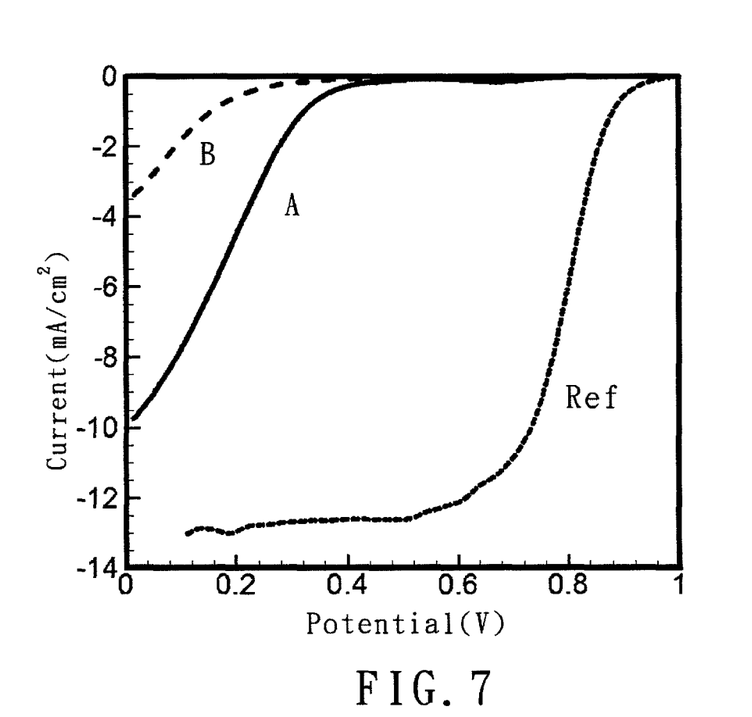
FIG. 7 is linear sweep voltammetry (LSV) curves of the iron oxide catalyst in accordance with the first and second examples and a third example of the present invention.

In addition, linear sweep voltammetry (LSV) curves of the iron oxide catalyst in accordance with a preferred embodiment of the present invention are shown in FIG. 7. From the relationship of potential vs. current, the onset electrode potential for oxygen reduction catalyzed by "B" catalyst is much more negative than that catalyzed by "A" catalyst; so that the electroatalytic activity of "A" catalyst is superior to that of "B" catalyst.

Figure 8:
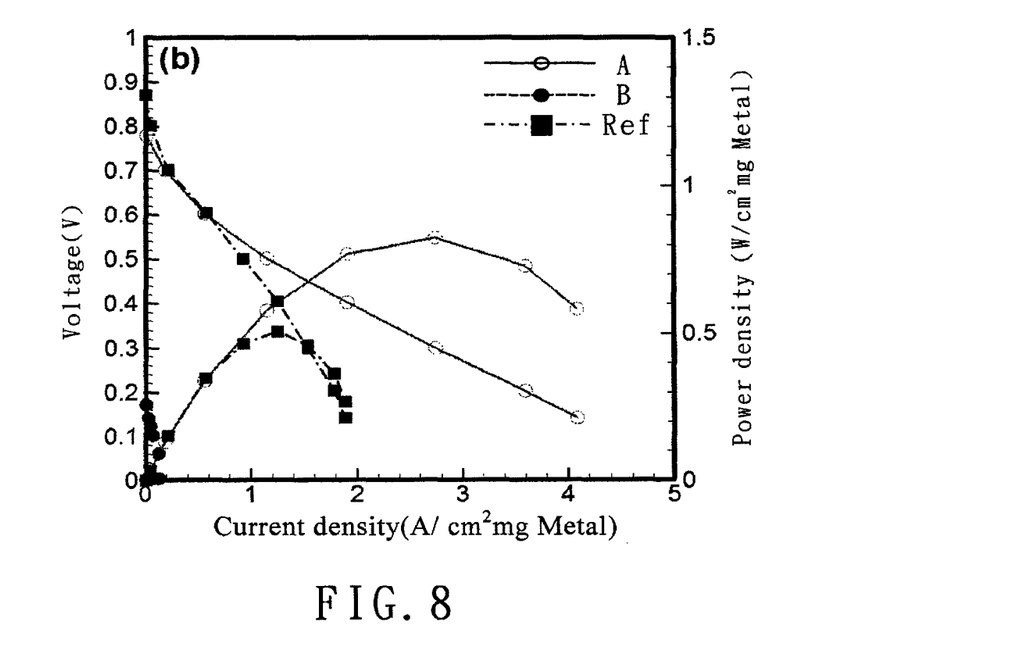
FIG. 8 is a diagram of voltage and power density vs. current density curves of the FIG. 7.

I. Testing for a Single Cell:

For measuring performance of MEA, single cell operates MEA in 0.5V. Under 24 hours of operation in fuel cell, a stable current density and polarization curves can be obtained. Active area of fuel cell is 5 cm². 0.4 mg, 20 wt. % of Pt/C-ETEK is loaded in anode catalyst. 0.08 mg of "A" catalyst, 0.08 mg of "B" catalyst, and 0.4 mg of Pt/C-ETEK is loaded in cathode catalyst. Flow rate of fuel, $H_2$ is 200 mL/min. Flow rate of oxidant, air is 300 mL/min. Temperature of operation is 36□. As a result, FIG. 8 shows that performance of membrane electrode assembly (MEAs) with the "A" catalyst cathode is better than with the "B" catalyst cathode. This can be attributed to the enhanced activity for ORR, in agreement with the composition of the catalyst that magnetite ($Fe_3O_4$) co-existed with hematite ($Fe_2O_3$). Furthermore, normalized power density of "A" catalyst is larger than that of commercial 20 wt. % Pt/C-ETEK (Ref.).

Figure 9:
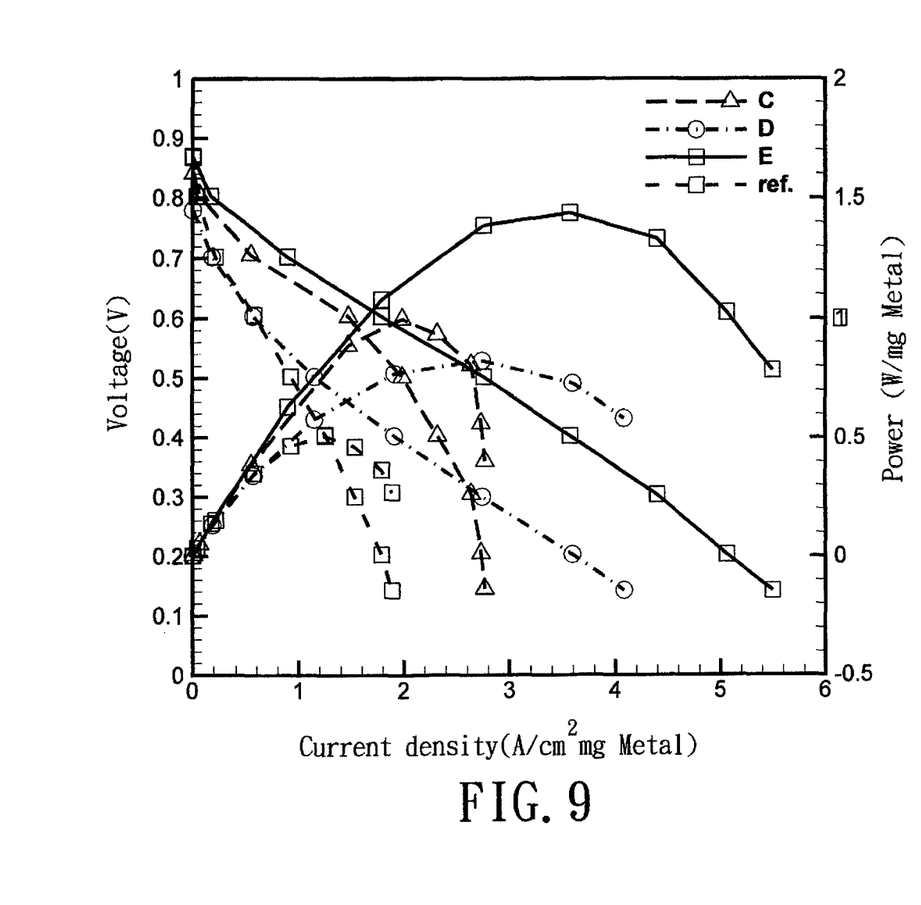
FIG. 9 is a diagram of voltage and power density vs. current density curves of the iron oxide catalyst in accordance with the third example and fourth and fifth examples of the present invention.

In addition, referring to FIG. 9, 0.4 mg, 20 wt. % of Pt/C-ETEK is loaded in anode catalyst. 0.08 mg of "C" catalyst, 0.08 mg of "D" catalyst, 0.08 mg of "E" catalyst, and 0.4 mg of Pt/C-ETEK is loaded in cathode catalyst respectively wherein formation of "C" catalyst, "D" catalyst, and "E" catalyst are obtained respectively from the third to the fifth examples according to the preferred teachings of the present invention. As a result, from comparison of current density and polarization curves, performance of $Fe_3O_4$/C is better than that of commercial 20 wt. % Pt/C-ETEK (Ref.).

Figure 10:
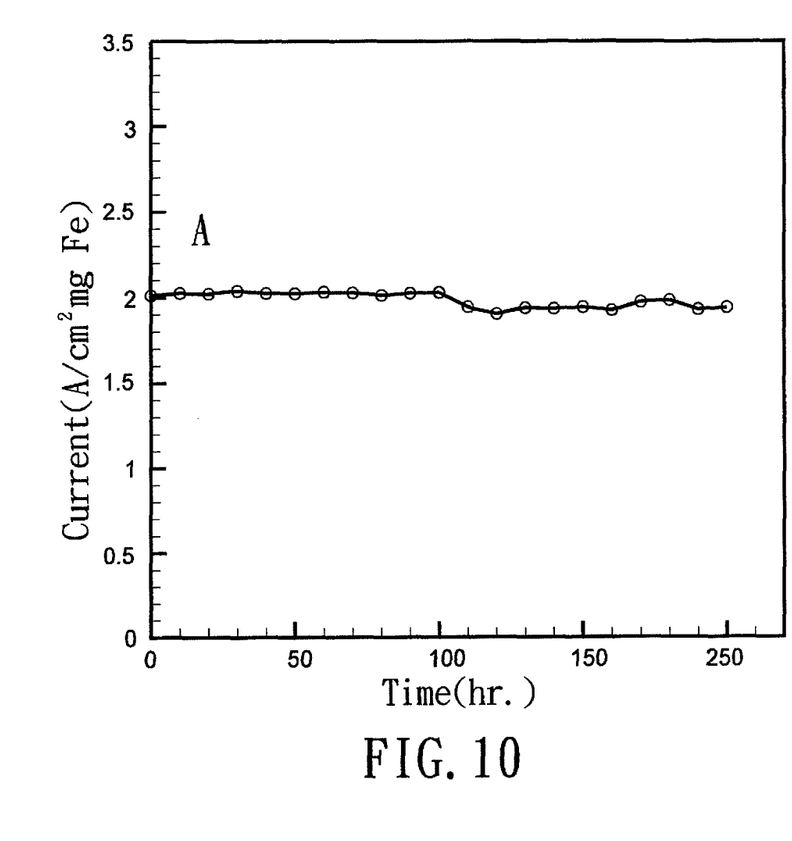
FIG. 10 is a diagram for stability test in accordance with the first example of the present invention.

In addition, referring to FIG. 10, the stability of the "A" catalyst ($Fe_3O_4$/C-en) of the present invention is quite stable. Please referring to reference of S.-J. Liu, C.-H. Huang, C.-K. Huang, W.-S. Hwang, Chem. Comm. (2009) for more related testing results.

The manufacturing method of the iron oxide catalyst ($Fe_3O_4$/C) through iron complex is to incorporate iron oxide into carbon black, which is better to be Vulcan XC-72 carbon black. $Fe_3O_4$/C shows promising electrocatalytic activity for ORR in PEMFC. The current density measured with the iron oxide catalyst which only contains 2 wt. % Fe according to the preferred teachings of the present invention is already about ½ of that measured with a commercial Pt-based catalyst containing 20 wt % metal loading. The normalized current density of $Fe_3O_4$/C is much larger than that of the 20 wt. % Pt/C-ETEK. Furthermore, due to Fe ions are reacted with the at least one chelating agent to form iron complex first before formation of catalyst, activity and the ability of catalysis of the iron oxide catalyst ($Fe_3O_4$/C) can be enhanced.

Thus since the invention disclosed herein may be embodied in other specific forms without departing from the spirit or general characteristics thereof, some of which forms have been indicated, the examples described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A manufacturing method of making an iron oxide through an iron complex, comprising:
   a chelating step mixing a ferric chloride, first chelating agent and second chelating agent with a solvent to form an iron complex solution, wherein the first and second chelating agents are selected from a group consisting of ethylenediamine, 1,10-phenanthroline, 2,2'-Bipyridine, diethylenetriamine, triethylenetetraamine, phenanthroline, and bipyridine, and $Fe^{3+}$ ions of ferric chloride being reacted with the first and second chelating agent to form the iron complex;
   a drying step removing the solvent from the iron complex solution to obtain a dried iron complex; and
   a heat treatment step executing heat treatment for the dried iron complex to form iron oxide with molecular formula $Fe_3O_4$, wherein the heat treatment step is processed under a nitrogen atmosphere;
   wherein the iron complex is in the form of $Fe[R_1]_a[R_2]_b[H_2O]_c^{3+}$, with the $R_1$ representing the first chelating agent and the $R_2$ representing the second chelating agent and being different from the first chelating agent, wherein an equation of (a ×the coordination number of $R_1$)+(b×the coordination number of $R_2$)+c=6 is held and a, b and c are not zero.

2. The manufacturing method of making the iron oxide through the iron complex as defined in claim 1, wherein the ferric chloride and the first and second chelating agents are mixed with the solvent by continuously stirring.

3. The manufacturing method of making the iron oxide through the iron complex as defined in claim 1, wherein the solvent is sonicated after ferric chloride and the first and second chelating agent are added into the solvent.

4. The manufacturing method of making the iron oxide through the iron complex as defined in claim 3, wherein the solvent containing the iron complex is sonicated for 24 hours.

5. The manufacturing method of making the iron oxide through the iron complex as defined in claim 1, wherein the drying step is processed under vacuum condition.

6. The manufacturing method of making the iron oxide through the iron complex as defined in claim 1, wherein the temperature for processing the heat treatment step is limited between 800 and 900° C.

7. The manufacturing method of making the iron oxide through the iron complex as defined in claim 1, wherein a time period for processing the heat treatment step is 1 to 4 hours.

8. The manufacturing method of making the iron oxide through the iron complex as defined in claim 1, wherein after completing the heat treatment step, iron oxide is allowed to cool to room temperature in a nitrogen atmosphere.

* * * * *